United States Patent [19]

Jarrett, Jr.

[11] Patent Number: 5,068,799
[45] Date of Patent: Nov. 26, 1991

[54] SYSTEM AND METHOD FOR DETECTING FLAWS IN CONTINUOUS WEB MATERIALS

[76] Inventor: Harold M. Jarrett, Jr., 450 Barkshire La., Roswell, Ga. 30075

[21] Appl. No.: 726,529

[22] Filed: Apr. 24, 1985

[51] Int. Cl.⁵ .............................................. G01N 21/88
[52] U.S. Cl. .................... 364/507; 364/572; 364/724.01; 382/31; 356/430; 356/238; 356/239
[58] Field of Search ............... 364/507, 900, 551, 552, 364/570, 572, 724, 726; 324/238, 240; 356/429, 430, 431, 237, 238, 239; 382/30, 31

[56] References Cited

U.S. PATENT DOCUMENTS

| | | | |
|---|---|---|---|
| 3,665,419 | 5/1972 | Hartmann et al. | 364/200 |
| 3,877,821 | 4/1975 | Price et al. | 356/237 |
| 3,900,265 | 8/1975 | Merlen et al. | 364/507 |
| 3,944,978 | 3/1976 | Jensen et al. | 382/31 |
| 3,950,635 | 4/1976 | Constant | 364/724 |
| 3,980,891 | 9/1976 | Slaker | 356/431 |
| 4,044,241 | 8/1977 | Hatley, Jr. | 333/18 |
| 4,118,127 | 10/1978 | Klein et al. | 356/237 |
| 4,247,204 | 1/1981 | Merlen et al. | 356/431 |
| 4,547,800 | 10/1985 | Masaki | 382/30 |
| 4,561,104 | 12/1985 | Martin | 356/237 |

FOREIGN PATENT DOCUMENTS 0008384 1/1983 Japan ..................................... 382/65

OTHER PUBLICATIONS

Rose et al., "Flaw Classification in Welded Plates Using a Microprocessor Controlled Flaw Detector", 1980, pp. 159–164.

Vander-Ingt, "Signal Detection by Complex Spatial Filtering", Apr. 1964, pp. 139–145.

Winzer et al., "Improved Holographic Matched Filter Systems for Pattern Recognition . . . ", Oct. 1972, pp. 222–227.

Couchman et al., "Computerized Signal Processing for Detecting Cracks Under Installed Fasteners", Nov. 1976, pp. 256–262.

*Primary Examiner*—Parshotam S. Lall
*Assistant Examiner*—V. N. Trans
*Attorney, Agent, or Firm*—Kenneth W. Float

[57] ABSTRACT

A method and apparatus for detecting flaws in continuous web material illuminated by a light source and optically scanned to produce a digitalized electronic image of said material. The digitized image data representative of the continuous web material is stored in memory. The image data is also applied to a digital signal processor which identifies areas of the image which represent potential flawed areas of the continuous web material. A variety of spatial matched filters are employed to detect the flaws. Information concerning the locations of the potential flaws is transferred to a computer which analyzes in detail portions of the stored image in the vicinity of the identified areas. The processing performed in the computer verifies the presence of flaws in the material.

15 Claims, 2 Drawing Sheets

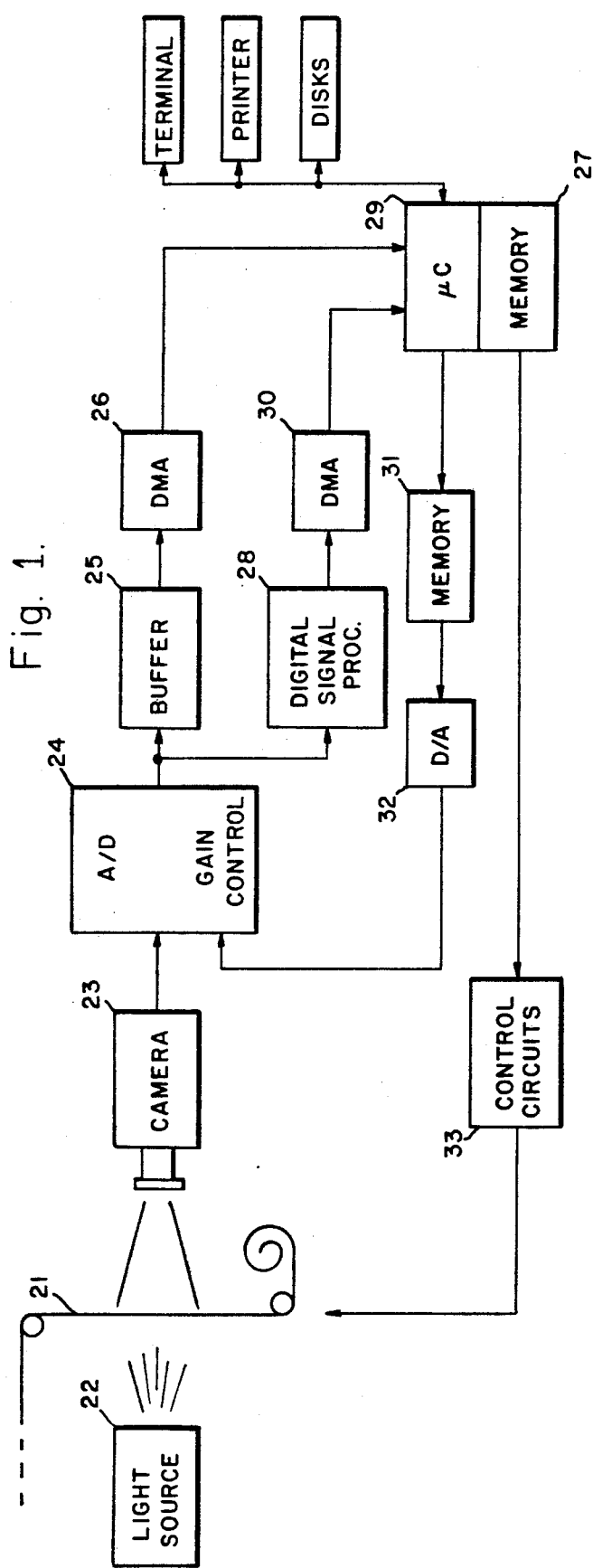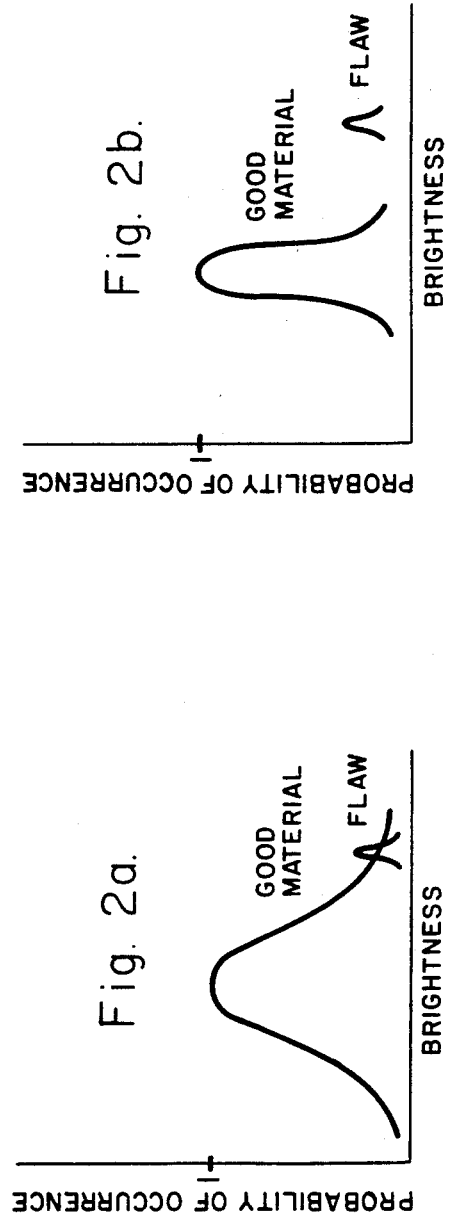

SYSTEM AND METHOD FOR DETECTING FLAWS IN CONTINUOUS WEB MATERIALS

BACKGROUND

The present invention relates generally to inspection systems and methods for detecting flaws in continuous web materials, and more particularly, to such systems and methods which employ digital signal processing techniques to detect the flaws.

The inspection of continuous web materials, such as carpet and cloth, and the like, are time consuming, laborious processes. Typically, these operations are performed manually by inspectors who observe the woven or tufted material as it moves past an inspection station. This is a very tedious job, and the quality of the inspection is difficult to control, due to such human factors as eye strain and fatigue.

Consequently, automatic inspection systems have been designed to detect flaws in these materials as they are being produced. For example, a basic system is disclosed in U.S. Pat. No. 3,135,867, entitled "Apparatus for Inspecting a Moving Web." This patent discloses a system which uses a light source to illuminate a moving web and a photomultiplier light detector and mirror arrangement for scanning the moving web. The output of the photomultiplier is thresholded and any signals exceeding the threshold are identified as flaws.

U.S. Pat. No. 4,124,300, entitled "Method for Automatic Fabric Inspection" discloses a system which employs a laser to irradiate moving web material. Diffraction patterns created by the interaction of the laser light and the material are analyzed to produce data indicative of the quality of the material.

U.S. Pat. No. 4,232,336, entitled "Inspection of Elongated Material" discloses a method of inspecting materials to determine the presence of surface irregularities. A video camera and processing circuitry are employed to analyze light and shadowed areas of the material illuminated with a high intensity strobe light. This invention takes advantage of high-contrast images created by the light/shadow interfaces to provide cues to the presence of flaws.

Although not related directly to the inspection of continuous web material, other inspection systems have been designed which employ image processing techniques to detect flaws of various kinds. For instance, U.S. Pat. No. 4,484,081, entitled "Defect Analysis System" discloses an inspection system employed in inspecting manufactured parts. This system employs a video imaging system and processing circuitry which includes thresholding and region growing circuitry to analyze the defects. The system assumes readily visible high signal-to-noise ratio images. The system analyzes binary images to identify regions of the image whose pixel intensities are above a predetermined threshold. These regions are then analyzed and compared with rejection criteria such as size, shape, direction and position, and the like.

U.S. Pat. No. 3,987,244, entitled "Programmable Image Processor" deals with a system that compares a video image of an object in the field of view to an image of a similar object stored in memory. The system provides an indication of the mismatches between the two images thus indicating misalignment of the subject object relative to orthogonal directions defined in the field of view.

U.S. Pat. No. 4,197,584, entitled "Optical Inspection System for Printing Flaw Detection" discloses a flaw detection system for use with currency printing. The system uses two cameras to scan a reference article and an item under test. The two images are electronically compared and difference signals are generated. A large difference signal is indicative of a flawed test item.

Therefore, although many systems have been designed to inspect continuous web material and other specialized items, all of the systems assume that the flaws to be detected are readily visible, in that the flaws have a high signal-to-noise ratio when viewed by a video camera, or the like.

The signal-to-noise problem in continuous web processing is a serious one due to the fast operating speeds of the machines employed to weave the materials. For example, in a typical production finishing operation for woven cloth, the cloth moves at a rate of eighty to two hundred yards per minute. This requires an extremely fast data processing system to detect and process the video information and output flaw detection data.

In general, the continuous web material, such as cloth and carpet, have a directional nature due to the orthogonal nature of the weaving and tufting process. Accordingly, the flaws that typically exist in the finished products are directional. Heretofore, no continuous web material inspection system has utilized the directional nature of the flaws to detect flaws.

Accordingly, it would be an improvement in the continuous web material inspection art to have an inspection system and method for inspecting moving continuous web material at high speed and provide flaw data for flaws which are normally not easily detected.

It would also be an improvement in the continuous web material inspection art to have an inspection system and method which takes advantage of the directional nature of the defects in the materials in order to detect heretofore undetectable flaws.

SUMMARY OF THE INVENTION

In order to overcome the limitations of prior art continuous web material inspection systems and methods, the present invention provides for a flaw detection method and system which incorporates high-speed digital signal processing techniques to analyze the flaws. The present invention comprises a system and method of detecting flaws in continuous web material which is illuminated and which is scanned by an optical scanning system to produce digitized output signals representative of the material. The present invention employs digital filtering techniques and methods utilizing spatial filtering to detect flaws in the material which are undetectable by conventional detection processes.

The most basic method in accordance with the present invention comprises processing the digitized output signals utilizing spatial filters to identify signals present therein which are representative of flaws in the material and generating output signals indicative of the locations of the flaws in the material. This processing generally comprises using matched filters corresponding to flaw patterns known to be present in the material to assist in identifying the flaws. The potential flaw locations are stored in memory and analyzed to verify the existence of flaws at the identified locations.

A more detailed statement of one method of the present invention comprises applying the digitized output signals to a digital signal processor and storing them in a memory. The signals applied to the digital signal processor are processed by matched filters to identify locations in the memory which contain data representing potential flaws. A computer then analyzes the stored signals identified by the signal processor as those representing potential flaws to verify the existence of the flaws.

The system in accordance with the principles of the present invention is designed to detect flaws in continuous web material which is illuminated and which is scanned by an optical scanning system to produce digitized output signals representative of the material. The improvement provided by the present invention comprises a digital signal processor which implements predetermined spatial filters to more easily detect flaws. The signal processor processes the digitized output signals from the optical scanning system utilizing the spatial filters to identify signals present therein which are representative of flaws in the material. The processor also provides output signals indicative of the locations of the flaws in the material.

As part of the system, a memory is provided to store the digitized output signals and a first direct memory access controller is provided for transferring the digitized signals to the memory. A computer is provided for processing signals stored in the memory based upon signals derived from the digital signal processor which are indicative of locations in the memory which contain data representing potential flaws. The computer verifies the existence of actual flaws corresponding to identified memory locations.

More particularly, matched filtering techniques are employed in the digital signal processor to isolate potential flaws and the computer is cooperatively employed to provide detailed analysis and classification of the potential flaws as true flaws. The computer is also employed to control memory management functions, and input and output functions to peripherals, storage devices and a video display. In some applications, the general purpose computer may be adapted to control the production machinery to temporarily interrupt its operation while repairs to the woven material are made. In other applications, a printout of flaws may be provided, indicating their position and severity, to act as a quality control record for the processed material.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which:

FIG. 1 illustrates a system block diagram of an automatic inspection system for detecting flaws in continuous web material in accordance with the principles of the present invention;

FIGS. 2a and 2b show graphs which illustrate the benefits of using spatial filtering to detecting flaws.

DETAILED DESCRIPTION

Figure 3:
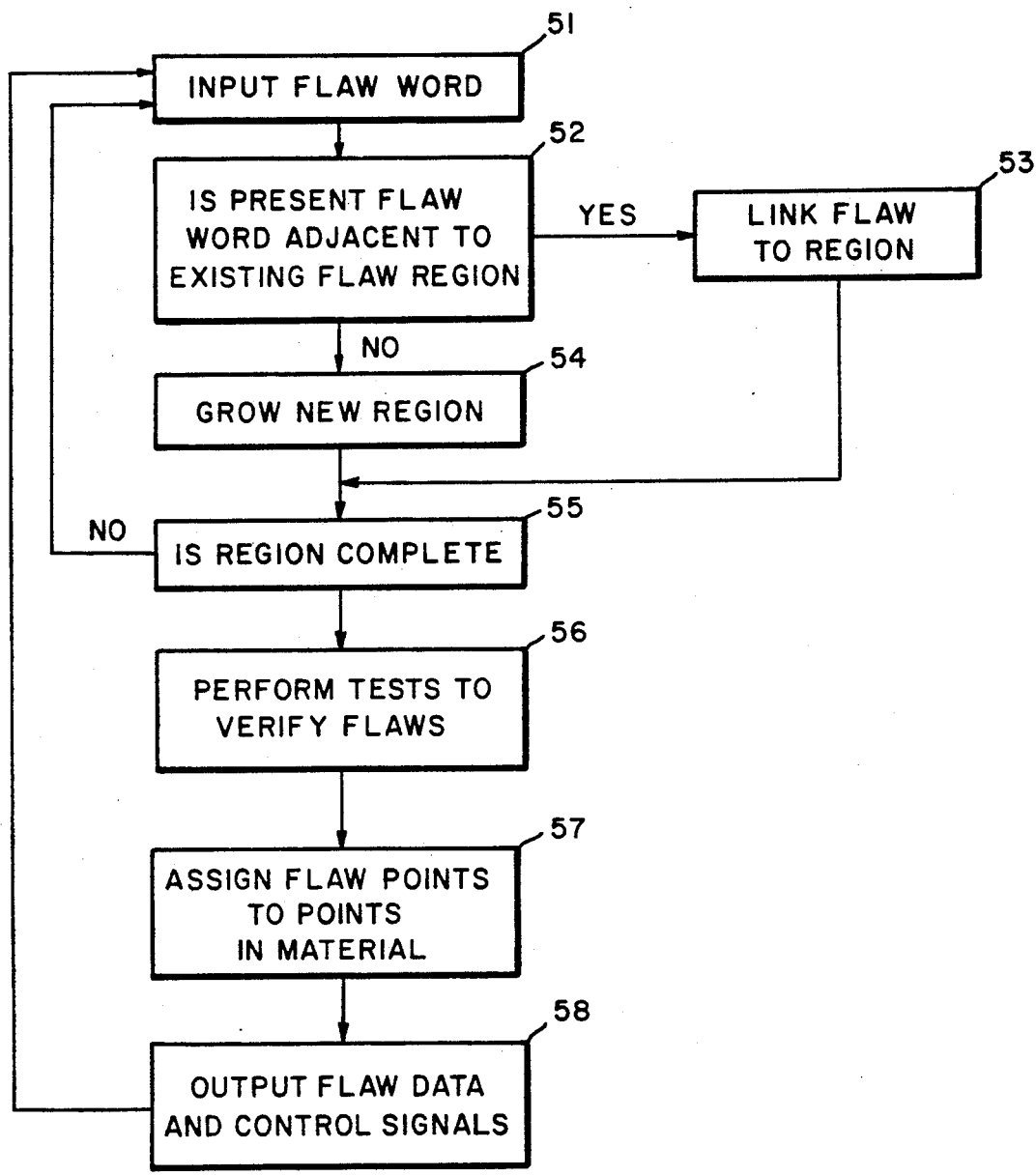
FIG. 3 shows a flow diagram illustrating the processing steps performed in the computer portion of the system of FIG. 1.

Referring to FIG. 1, a system block diagram of an automatic inspection system 20 for detecting flaws in continuous web material in accordance with the principles of the present invention is shown. A production machine (not shown) has produced a continuous web of material 21 which is provided for inspection by the inspection system 20. An illumination source 22, such as high intensity light is provided to back light the material 21. Alternatively, the material 21 may be illuminated from the front.

A video camera 23 is positioned to scan the material 21 as it moves past its field of view while the material 21 is being produced. The video camera 23 may typically operate in the visible light spectrum, but may also operate with x-rays, ultra-violet, near-infrared or far-infrared radiation. The video camera 23 typically provides an analog output signal, so an analog to digital converter 24 is coupled to the output of the video camera 23 to convert the camera's analog output signal to a digital signal. The analog to digital converter 24 may be a "flash" type analog to digital converter, which is faster than successive approximation analog to digital converters. This requirement is due to the fact that video data has a wide bandwidth.

A first-in, first-out (FIFO) buffer memory 25 is coupled to the output of the analog to digital converter 24 and is adapted to serially accumulate video data to allow asynchronous data transfer to the memory 25. The buffer memory 25 is shown by way of example, and may not be required in all applications. A first direct memory access controller 26 is coupled to the buffer memory 25 and is adapted to transfer video data accumulated in the buffer memory 25 to a random access memory (RAM) 27. The controller 26 is adapted to transfer the video data to the RAM 27 so that a "picture" of the video image seen by the video camera 23 is stored in the RAM 27. Accordingly, the serial video data stored in the buffer memory 25 converted to a predetermined number of rows of video data in the RAM 27 which corresponds to the video image.

The output of the analog to digital converter 24 is also coupled to a digital signal processor 28. The digital signal processor 28 is in turn coupled by way of a second direct memory access controller 30 to the RAM 27 and to a computer, such as a microcomputer 29. The digital signal processor 28 is adapted to analyze the video data on a real-time basis in order to provide for smoothing of the data, high and low-frequency filtering of the smoothed data, convolutional analysis of the smoothed data and statistical analysis of the image in random spatial vector directions within the image. The digital signal processor 28 is designed to provide high speed analysis capability of the video image in order to isolate potential flaws located in the processed material 21.

The processed data from the digital signal processor 28 is transferred to the microcomputer 29 and the RAM 27 under the control of a second direct memory access controller 30. The microcomputer 29 is adapted to provide a detailed analysis of the image stored in the RAM 27 in the vicinity of those points and areas identified by the digital signal processor 28. Typically, the microcomputer 29 employs computer programs to analyze the video data. These programs process the video data much more slowly than the signal processor 28, but operate on a much smaller volume of data, so that its relatively slow computational speed is not a drawback to the system 20.

The microcomputer 29 is also coupled to a second memory 31, which may be part of the RAM 27, and to a digital to analog converter 32, which in turn is coupled to the analog to digital converter 24. These components comprise an automatic calibration loop which is adapted to correct the processed digital data for variations in channel to channel output of the camera 23. This procedure is accomplished by means of a calibration procedure which loads the second memory 31 with data which is a function of the responsivity of the camera detectors when viewing non-flawed material. This data is combined with the video data processed during normal operation to normalize the output of the analog to digital converter 24. Alternatively, the normalization process may be accomplished digitally by employing a digital multiplier to multiply the output from the second memory 31 by the raw video data on a pixel by pixel basis prior to its application to the analog to digital converter 24.

In addition, the microcomputer 29 may be coupled to one or more terminals 33, printers 34, and floppy or hard disk storage devices 35 in order to provide operator interface and data output for operator action. In some applications, the microcomputer 29 may also be coupled to machine control circuitry 36 which in turn is coupled to the production machine. The microcomputer 29 is then adapted to provide control signals to the machine control circuitry 36 to stop the production machine to permit repair of the machine or the material, as the case may be.

In operation, the system 20 of the present invention operates as follows. The production machinery finishes cloth at a rate of between eighty and two hundred yards per minute, for example. The woven cloth is passed through the inspection area where it is illuminated by means of the illumination source 22 and viewed by the video camera 23. A typical video camera for use in the system 20 of the present invention may be a charge coupled device (CCD) camera manufactured by Radio Corporation of America, General Electric, Fairchild or Reticon, or the like. The cameras manufactured by these companies are line scan cameras which view the moving continuous web material to produce a continuous image of the material 21.

The video output of the camera 23 is converted to a digital signal by the analog to digital converter 24 and accumulated in the buffer memory 25. A typical analog to digital converter is model number 1014J manufactured by TRW, Incorporated and a model C67401 buffer manufactured by Monolithic Microsystems, Inc. is representative of the FIFO buffer memory 25 which may be employed in the present invention. The signals stored in the second memory 31 are converted to analog signals by the digital to analog converter 32 and applied to a reference voltage input in the analog to digital converter 24. Thus, the output of the analog to digital converter 24 is normalized on a pixel by pixel basis. After each pixel is clocked out of the video camera 23, the first direct memory access controller 26 transmits a DMA request pulse, and the data stored in the buffer memory 25 is transferred to the RAM 27 under control of the first direct memory access controller 26. The controller 26 transfers the video data to the memory 27 at high speed and stores the data in locations representative of the parallel rows of data corresponding to the video image seen by the camera 23. Thus, a "picture" is present in the RAM 27 corresponding to the video image seen by the camera 23 during any particular frame time.

The digital signal processor 28 operates on the video data to convert the noisy, raw video data into smoothed, filtered data that makes the flaws present in the material more observable. Hence, the signal processor 28 operates to increase the signal-to-noise ratio of the flawed areas of the material relative to the non-flawed areas. The various processing operations performed by the digital signal processor 28 will be described in more detail hereinbelow. In particular, the signal processor 28 is adapted to identify flaws not otherwise detectable by conventional inspection methods.

A better understanding of the present invention will be had from an understanding of the theory of spatial filtering as applied to flaw detection of moving continuous web materials. Assume that a video image is constructed due to the movement of material in front of a camera comprised of an array of detectors. In order to detect flaws having an extent of one thread width in the X or Y directions, the X and Y dimensions of the detectors must correspond to the thread width. Flaws are generally several detectors wide or tall, and since the material is comprised of X and Y directed threads, the flaws are also so directed.

The point to point (pixel to pixel) brightness of the image varies widely due to the randomness of the texture of the material. This implies that the standard deviation of the brightness distribution of the material is relatively large. Thus, there are many points in the field of view of the camera which vary substantially from the mean brightness of the field. The variation of a flawed pixel may be less severe than a naturally occurring random variation of good material. These facts highlight the problem with conventional methods of simple thresholding in detection of flaws in continuous web materials. Conventional systems have been unable to detect these flaws. This is illustrated in FIG. 2a, which shows a graph of probability of occurrence versus brightness level for a typical material illuminated and detected by conventional techniques.

However, by averaging some number of adjacent pixels, the average is a better approximation of the true mean of the brightness of the material as compared with one single pixel. Therefore, by replacing each pixel value in the field of view with the average of eight adjacent pixels, for example, and examining the distribution, the standard deviation of the filtered (average) distribution is less than that of the original. If an adequate number of pixels are averaged, the overlap of the flaw and good material distributions can be reduced. This is illustrated in FIG. 2b. Therefore, the flaws can be detected by thresholding without the false alarms which occur in conventional systems, and depicted in FIG. 2a.

In order to increase the signal-to-noise ratio of the flawed areas of the material 21, the signal processor 28 employs conventional smoothing and high and low-frequency filtering techniques to the stored data. Typically, the types of flaws may be categorized into several groups and these groups have known signatures which can be detected by means of match filtering techniques. The flaws generally show up as density variations of varying size and shape. The density variation causes the average brightness over the length of the flaw to vary. There may be a large amount of noise from point to point in the image, but the average brightness level is different in flawed and non-flawed areas. Therefore, averaging the signals in the direction of the flaws over the length of the flaws permits the detection of the flaws where conventional threshold detection techniques cannot.

Accordingly, the digital signal processor 28 contains spatial filters that average a predetermined number of adjacent pixels in the horizontal and vertical directions to increase the signal to noise ratio of the flaws. For example one filter may average three pixels in each direction from a particular pixel and replace the particular pixel with the computed average value. This operation is performed in both the horizontal and vertical directions. The result is a smoothing of the video data such that the signal plus noise is reduced to the average value of the signal across the image. This, in effect, highlights the flaws present in the image. In addition, this averaging technique may be applied to area, linear dimension, or linear non-orthogonal or other random shape analyses, as the situation may dictate. It is only necessary to identify the nature of the flaw and the appropriate filter shape corresponding to the flaw in order to isolate the flaw from the noise.

The signal processor 28 highlights the flaws present in the image and presents information to the microcomputer 29 in the form of cues. These cues contain information such as the memory location of areas which exceed threshold values, filtered video data and mean and standard deviation data for the image. The microcomputer 29 then analyzes the potentially flawed areas identified in the cue information by means of software programs which perform substantially the same analysis as that of the signal processor 28, but performs the tasks using software.

Typical of a microprocessor for use in the system of the present invention is model 80186 manufactured by Intel, Inc. or the like, or such other currently available computer chip such as those manufactured by Motorola, Inc., or the like.

The microcomputer 29 classifies the flaws and controls the peripheral devices attached thereto to permit operator interface with the system 20 and the production machine. Printouts contain a map of the flaws in the material 21 as well as data storage for archival purposes is provided under control of the microcomputer 29.

The processing operations performed in the signal processor 28 include horizontal and vertical non-recursive filtering and horizontal recursive filtering. The horizontal filter has the form $$HN = \sum_{i=1}^{n} a_i P(x - i, y),$$

where n is the number of samples in the filter kernel, $a_i$ is a shape coefficient, x is the horizontal location of the present pixel and y is the vertical location of the present pixel. For each pixel, the filtered value is equal to the sum of the prior "n" pixels, each multiplied by a coefficient.

The vertical non-recursive filter has the form $$VN = \sum_{i=1}^{n} a_i P(x, y - i),$$

where the parameters are as defined above.

The horizontal recursive filter has the form $$HR(x,y) = 1/n\ P(x,y) + (n-1)/n\ [HR(x-1,y)],$$

where the parameters are as defined above. This filter allows the use of very long filters without using large amounts of circuitry or memory. It is used for measuring slowly varying features such as average density or dye color changes, or the like.

FIG. 3 shows a flow diagram illustrating the processing steps performed in the microcomputer 29 of the system 20 of FIG. 1. These steps may be implemented by means of a computer program, or the like. The programming is such that a flaw word indicative of the location of the potential flaw is input as data to the program, as indicated in box 51. Then a determination is made whether or not the new flaw is adjacent to an existing flawed region, as indicated in box 52. If the flaw is adjacent to an existing flawed region, the flaw is linked to the region, as shown in box 53. If the flaw is not adjacent to any region, then a new region is constructed, as indicated in box 54.

If no new flaws are added to a region, a determination is made if the region is complete, as indicated in box 55. If the region is not complete, a new flaw word is input and the above processing is repeated until all the region is complete, as indicated in box 56. If the region is complete, verification tests are performed on the flawed regions, as indicated in box 57. These tests include checking the size of the region, and discarding any regions whose size is smaller than a predetermined limit. A determination is made whether the region is a line flaw or an area flaw. A regression line analysis may be performed to check the orthogonality of the points in the region. A "volume" analysis (area times brightness) may be performed. Thus, the regions are reviewed to determine whether or not the regions passed the above tests.

It is to be understood that region growing is generally well known in the signal processing art. For example, U.S. Pat. No. 4,484,081 discussed in the Background of the Invention section hereof discusses the concept of region growing in some detail.

Once the presence of the flaws has been determined, the flaw points are assigned to actual locations in the material. This may be accomplished by correlating the data with time and position data derived from a position motion sensor, or the like, located on the production machine. Finally, the data is provided to the operator in terms of a terminal display or print-out, and the data is archived in disk storage for future reference as indicated in box 58.

It is to be understood that the programming of the above-described flow diagram may be done by any person skilled in the programing art. Accordingly, the explicit program used to implement the flow diagram will not be described herein.

Accordingly, the flaw classification analysis is implemented in a versatile manner due to the software nature of the analysis mechanism. Modifications to the analysis performed in the microcomputer, including number and types of analysis performed, is implemented by means of software changes, and hence is quite adaptable to user requirements.

An improved method of detecting flaws in continuous web material that is illuminated by a light source and which is scanned by an optical scanning system to produce digitized output signals representative of the material in accordance with the principles of the present invention is described hereinbelow. The method comprises processing the digitized signals utilizing spatial filters to identify signals present therein which are representative of flaws in the continuous web material and generating output signals indicative of the locations of the flaws in the material.

More particularly, and in addition to the above steps, the accuracy of the flaw determination is verified by means of computer processing steps. The steps involve storing the digitized signals in memory, which provides a "picture" of the image therein, and then analyzing portions of the memory identified by the spatial filter processing steps to verify the existence of the flaws at those locations.

Thus, the present method provides a series of processing steps which determine the presence of flaws by means of spatial filtering techniques and then verifies the existence of those flaws at the identified locations. Fast digital matched filtering techniques are employed along with direct memory access techniques to permit processing of the flaws in the moving material. The digital image of the material is stored in memory while the spatial filtering process is performed and then the computer analyses only a portion of the memory locations to verify the flaws.

The present method also provides for analyzing unflawed material by means of the matched filters to provide calibration signals corresponding to each point in the image. The calibration signals are stored in memory and combined with the digital output signals analyzed by the processor to enhance the flaw detection process.

Thus, there has been described a new and improved system and method of detecting flaws in continuous web material. The system is automatic and is versatile owing to its programmable microcomputer hardware. In addition, the system is capable of detecting and classifying flaws heretofore undetectable by conventional inspection techniques. The method of the present invention provides for digital signal processing which isolates potential flaws in the material and a computer which verifies the existence of actual flaws at the points determined by the signal processor.

It is to be understood that the above-described embodiments are merely illustrative of some of the many specific embodiments which represent applications of the principles of the present invention. Clearly, numerous and varied other arrangements may be readily devised by those skilled in the art without departing from the spirit and scope of the invention.

What is claimed is:

1. A method of detecting flaws in continuous web material which is illuminated and which is scanned by an optical scanning system to produce digitized output signals representative of said material, said method comprising the steps of:
   processing said digitized output signals utilizing digital matched filters corresponding to flaw patterns known to be present in said material to identify signals present therein which are representative of flaws in said material; and
   generating first output signals indicative of the locations of said flaws in said material.

2. The method of claim 1 which further comprises the step of:
   processing said digitized output signals utilizing information contained in said first output signals which is indicative of potential flaw locations; and
   verifying the existence of flaws at said identified locations.

3. The method of claim 1 which further comprises the steps of:
   storing said digital output signals; and
   processing said stored signals and said first output signals to verify the existence of flaws in said material corresponding to locations in a memory which contain data representing potential flaws.

4. A method of detecting flaws in continuous web material which is illuminated and which is scanned by an optical scanning system to produce digitized output signals representative of said material, said method comprising the steps of:
   applying said digitized output signals representative of said material to a digital signal processor;
   storing said digitized output signals in a memory;
   processing said digitized output signals in said digital signal processor by means of digital matched filters corresponding to flaw patterns known to be present in said material to identify locations in said memory which contain data representing potential flaws; and
   processing signals stored in said memory and signals which have been identified by said digital signal processor as containing data representing potential flaws in said computer to verify the existence of flaws at those locations.

5. A method of detecting flaws in continuous web material which is illuminated and which is scanned by an optical scanning system to produce digitized output signals representative of said material, said method comprising the steps of:
   storing said digitized output signals in a memory;
   analyzing said digitized output signals by means of predetermined digital matched filters corresponding to predetermined flaw types to provide first output signals indicative of the locations of potential flaws in said material;
   analyzing in detail said stored digitized output signals at locations indicated by said first output signals to identify and classify actual flaws present at said locations in said material.

6. The method of claim 5 wherein the first analyzing step further comprises:
   analyzing unflawed material by means of said matched filters to provide calibration signals corresponding to each point in said material; and
   comparing output signals from said matched filters to said calibration signals to identify points in said stored image which correspond to potential flaws.

7. A system for detecting flaws in continuous web material which is illuminated and which is scanned by an optical scanning system to produce digitized output signals representative of said material, said system comprising:
   digital signal processing means comprising digital matched filters corresponding to flaw patterns known to be present in said material coupled to said optical scanning system for processing said digitized output signals utilizing said matched filters to identify signals present therein which are representative of flaws in said material, and for providing output signals indicative of the locations of said flaws in said material.

8. The system of claim 7 which further comprises:
   microprocessor means coupled to said digital signal processing means for process said digitized output signals utilizing information contained in said output signals which is indicative of potential flaw locations, an for verifying the existence of flaws at said identified locations.

9. The system of claim 7 which further comprises:
   microprocessor means, including memory means for storing said digitized output signals, coupled to said digital signal processing means for storing said digital output signals and for processing said stored signals and information contained in said output signals which are indicative of locations in said memory which contain data representing potential flaws, and for verifying the existence of flaws in said material corresponding to said identified memory locations.

10. A system for detecting flaws in continuous web material which is illuminated and which is scanned by an optical scanning system to produce digitized output signals representative of said material, said system comprising:
   memory means for storing said digitized output signals;
   digital signal processing means for processing applied digitized output signals by means of digital matched filters corresponding to flaw patterns known to be present in said material to identify locations in said memory which contain data representing potential flaws;
   controller means for transferring said digitized output signals to said memory and to said digital signal processor; and
   computer means, for processing signals stored in said memory means in accordance with output signals derived form said digital signal processing means which are indicative of locations in said memory which contain data representing potential flaws, and for verifying the existence of flaws at said identified memory locations.

11. A method of detecting flaws in continuous web material which is illuminated and which is scanned by an optical scanning system to produce digitized output signals representative of said material, said method comprising the steps of:
   analyzing unflawed material by means of digital matched filters to provide calibration signals corresponding to said unflawed material;
   storing said calibration signals in a first portion of a memory;
   storing said digitized output signals in a second portion of said memory;
   processing said digitized output signals by means of said digital matched filters to generate flaw location signals indicative of potential flaws locations in said material; and
   processing said digitized output signals stored in said second portion of said memory and said calibration signals stored in said first portion of said memory by means of a computer in regions surrounding said potential flaw locations by comparing said digitized output signals to said calibration signals in order to verify the existence of flaws at those locations.

12. A method of detecting flaws in continuous web material which is illuminated an which is scanned by an optical scanning system to produce digitized output signals representative of said material, said method comprising the steps of:
   analyzing unflawed material by means of digital matched filters corresponding to predetermined flaw types to provide calibration signals corresponding to said material;
   storing said calibration signals in memory;
   analyzing said digitized output signals by means of said digital matched filters to provide first output signals;
   comparing said first output signals to said calibration signals to identify locations in said material which correspond to potential flaws; and
   re-analyzing said digitized output signals at said identified locations to verify and classify actual flaws present at said locations in said material.

13. A system for detecting flaws in continuous web material which is illuminated and which is scanned by an optical scanning system to produce digitized output signals representative of said material, said system comprising:
   digital signal processing means comprising predetermined digital matched filters coupled to said optical scanning system for processing said digitized output signals utilizing said filters to identify signals present therein which are representative of flaws in said material, and for providing output signals indicative of the locations of said flaws in said material; and
   microprocessor means coupled to said digital signal processing means for processing said digitized output signals utilizing information contained in said output signals which is indicative of potential flaw locations, and for verifying the existence of flaws at said identified locations.

14. A system for detecting flaws in continuous web material which is illuminated an which is scanned by an optical scanning system to produce digitized output signals representative of said material, said system comprising:
   digital signal processing means comprising predetermined digital matched filters coupled to said optical scanning system for processing said digitized output signals utilizing said filters to identify signals present therein which are representative of flaws in said material, and for providing output signals indicative of the locations of said flaws in said material; and
   microprocessor means, including memory means for storing said digitized output signals, coupled to said digital signal processing means for storing said digital output signals and for processing said stored signals and information contained in said output signals which are indicative of locations in said memory which contain data representing potential flaws, and for verifying the existence of flaws in said material corresponding to said identified memory locations.

15. A system for detecting flaws in continuous web material which is illuminated an which is scanned by an optical scanning system to produce digitized output signals representative of said material, said system comprising:
   digital signal processing means comprising digital matched filters for processing unflawed material to provide calibration signals corresponding thereto and for processing said digitized output signals to generate flaw location signals indicative of potential flaw locations in said continuous web material;
   first memory means for storing said calibration signals;
   second memory means for storing said digitized output signals; and
   computer means for processing said digitized output signals stored in said second memory means in regions surrounding said potential flaw locations by comparing said digitized output signals to said calibration signals in order to verify the existence of flaws at those locations.

* * * * *